United States Patent [19]

Allen

[11] Patent Number: 4,731,077
[45] Date of Patent: Mar. 15, 1988

[54] UNIVERSAL IMPLANT FOR ARTIFICIAL EYES

[76] Inventor: Edwin L. Allen, 1192 E. Jefferson, Iowa City, Iowa 52240

[21] Appl. No.: 66,312

[22] Filed: Jun. 25, 1987

[51] Int. Cl.⁴ .............................................. A61F 2/14
[52] U.S. Cl. .................................................... 623/4
[58] Field of Search ..................... 623/4; 446/389, 392

[56] References Cited

U.S. PATENT DOCUMENTS

| | | | |
|---|---|---|---|
| 2,574,750 | 11/1951 | Moore | 623/4 |
| 2,653,327 | 9/1953 | Allen et al. | 623/4 |
| 3,070,808 | 1/1963 | Allen | 623/4 |
| 3,436,763 | 4/1969 | Milauskas | 623/4 |

*Primary Examiner*—Ronald L. Frinks
*Attorney, Agent, or Firm*—James C. Nemmers

[57] ABSTRACT

An improved implant for replacing volume and transmitting motility from the remaining eye muscles to artificial eyes after eye removal. As compared to earlier implants, the mass has been redistributed which makes the implant safer and the tissues around the implant and prosthetic eye more natural appearing. The mounds of the implant are lower and more rounded, and the main body of the implant is less spherical so as to more accurately and completely fill the void left in the equatorial region around the implant by an enucleated eye. The implant remains short in the anterior-posterior dimension thereby leaving adequate space for a cosmetic prosthetic eye. Also, the implant is provided with suture holes to provide for improved surgical techniques for permanently retaining the implant in place.

4 Claims, 14 Drawing Figures

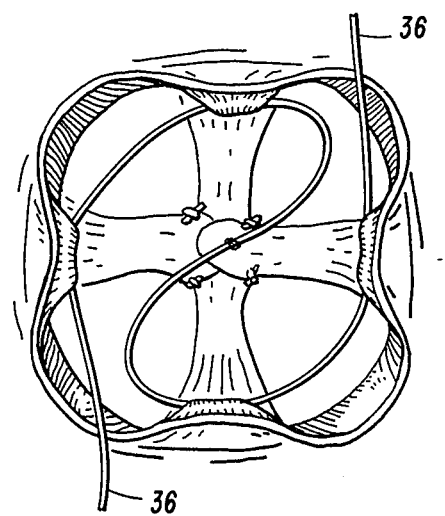
FIG 12

FIG 14
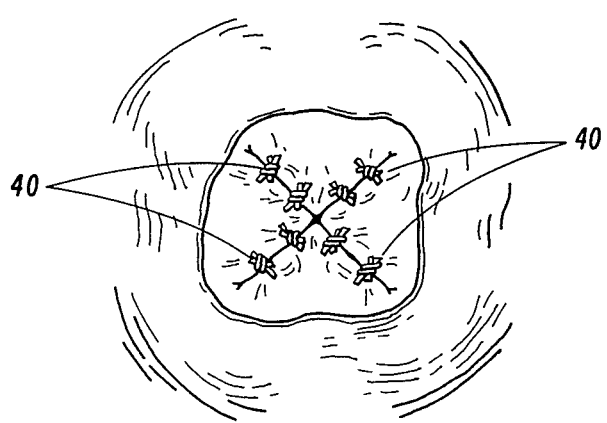

UNIVERSAL IMPLANT FOR ARTIFICIAL EYES

BACKGROUND OF THE INVENTION

While completely spherical implants have long been used by surgeons for replacing lost volume following eye removal, the shape of the front, convex surface that is presented through the covering tissues acts like a ball and socket joint with the related concave posterior surface of the artificial eye. Therefore, slippage is allowed between the eye socket tissues covering the spherical implant and the posterior spherically concave surface of the prosthetic eye. Obviously, a person who has lost an eye desires the best cosmetic replacement, including the best possible correlation of movement with the remaining living eye. To that end, what has been called the "Iowa Implant" was developed and is disclosed in U.S. Pat. No. 3,070,808 issued Jan. 1, 1963 to Edwin Lee Allen for his invention entitled "Eyeball Replacement Buried Muscle Cone Motility Implant Body with Post-Surgical Conformer Prosthesis". The Iowa Implant resulted in a reduction in the number of cases exhibiting droop in the lower and upper eyelids due to support of the prosthesis on the mounds of the implant, and because the prosthesis is keyed to the implant rather than being free to slip, torsional end-point movement was likewise reduced.

In the hands of surgeons who see the merits of the Iowa Implant, it has proven successful in all respects in almost all cases. However, the majority of eye surgeons mistakenly believe the prominent mounds of the implant will very often erode through the covering tissues and result in extrusion. This belief, along with the time consuming surgical techniques required of implantation have been the major criticisms of quasi-integrated implants such as the Iowa Implant. As a result, the spherical (or ball) implant has become the implant of choice of most surgeons.

Therefore, there is a need for an improved implant that will assure successful retention, remove the concerns of possible extrusion and make the surgical procedur e for implantation shorter and more simple. Any such improved implant should also result in a more natural appearance without sacrificing motility.

SUMMARY OF THE INVENTION

The implant of the invention is an improved version of the Iowa Implant in that the mass of the implant is redistributed by making the mounds on the interior surface lower, more rounded and farther apart. The implant is thus broader equatorially so that there is produced a fuller upper eyelid fold resulting a more natural appearance. This broader configuration also provides a better leverage effect on the prosthesis. The improved implant of the invention also incorporates central, crossed tunnels in the anterior aspect of the implant and suture holes at the base of and through the mounds to facilitate simplied surgical techniques. With the implant of the invention, the surgeon does not need to clean and tag the muscles or meticulously imbricate them over the implant. Vertical and horizontal valleys crossing on the implant's anterior surface are to accommodate the rectus muscles and allow their imbrication at the point of crossing.

BRIEF DESCRIPTION OF THE DRAWINGS

FIGS. 12, 13 and 14 are views illustrating the cruxiate closure, an alternate surgical procedure in which the Tenon's capsule is distributed over the implant and sutured closed.

DESCRIPTION OF THE PREFERRED EMBODIMENT OF THE INVENTION

Figure 1:
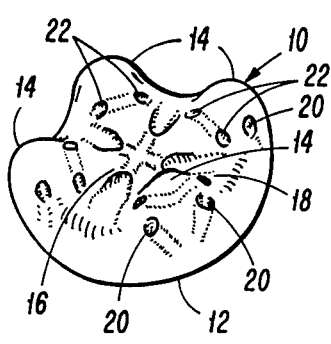
FIG. 1 is a perspective view showing primarily the anterior surface and mounds of the implant of the invention.

The implant body designated generally by the reference numeral 10 is preferably compression-molded of methylmethacrylate resin. The implant preferably is made in three sizes--small, medium and large. The implant has a convex hemispherical posterior surface 12 with a radius of 12.5 mm for the large size, 12.0 mm for the medium size and 11.5 mm for the small size. This posterior surface 12 provides a smooth surface that facilitates movement in the human eye socket.

Figure 2:
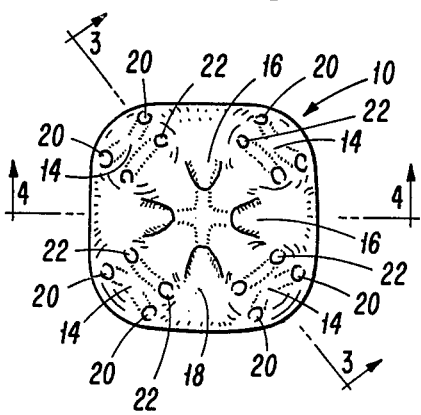
FIG. 2 is a plan view of the anterior surface of the implant.
Figure 3:
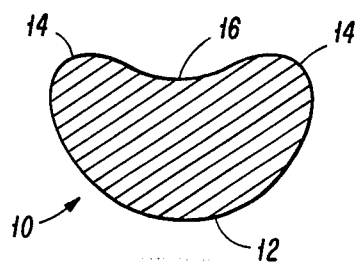
FIG. 3 is a sectional view of the implant taken on line 3—3 of FIG. 2 but omitting the openings.
Figure 4:
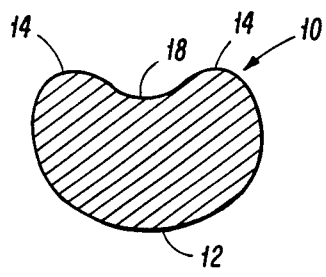
FIG. 4 is a sectional view of the implant taken on the line 4—4 of FIG. 2 but omitting the openings.

The implant is for use with a prosthetic eye and comprises a main body 10 having top and bottom edges that are straight across and parallel to each other joined by rounded corners to sides that are straight and parallel to each other to form a substantially square configuration having an anterior portion as best shown in FIG. 2 and a smooth convex posterior surface 12 as shown in FIG. 1.

The anterior portion of the body 10 is provided with a plurality of circumferentially spaced, outwardly tapered mounds 14, four such mounds being shown in the preferred embodiment one at each corner of the body 10. The mounds 14 are formed integrally with the body 10 and terminate in a rounded extremity. The anterior portion of the body 10 between the mounds 14 provides slightly concave surfaces or shallow valleys 16 and 18 for receiving the severed rectus muscles of a human eye together with the Tenon's capsule and conjunctiva as described more fully hereinafter.

One valley extends between the top and bottom edges and the other valley extends between the sides of the main body 10 with the two valleys 16 and 18 crossing at the center of the anterior portion to form a relatively flat central portion. A pair of interconnected suture receiving holes are formed in each of the valleys in the central portion to receive sutures 26 used to secure the ends of the rectus muscles 28 and 30 to each other and to the implant as shown in FIGS. 5-8.

When the implant of the invention is secured in place, the valley 16 will be oriented vertically while the valley 18 will be oriented horizontally. The narrowest measurement across the body 10 is parallel with the valleys 16 and 18, and measures 20.0 mm for the large, 19.5 mm for the medium and 18.0 mm for the small implant. The widest dimension is measured diagonally across the mounds 14 and is 24.0 mm for the large size, 23.0 mm for the medium size and 22.0 mm for the small size.

The overall dimension from the top of the mounds 14 to the posterior surface 12 is 15.0 mm for the large, 14.0 mm for the medium and 12.0 mm for the small size implant, 2.4 mm for the medium size and 2.0 mm for the small size implant.

Openings 20 are formed along the exterior surface of the mounds 14, two such openings 20 being shown for each mound. These openings extend downwardly and inwardly toward each other as best seen in FIG. 1. The openings 20 provide tunnels for fibrous tissue to grow into thus producing a firm interweaving between the implant and Tenon's capsule and muscle sheaths. The openings 20 also can be used for the reception of devices for supporting the implant temporarily during the implantation surgery, although such techniques are more complex and generally not employed. For example, openings 20 can be used for the insertion of Ferguson clips, which are stainless steel clips that have been used routinely with the Iowa Implant. However, because of the improved surgical procedures permitted by use of the implant of the invention, it is doubtful whether techniques similar to those employed with the Iowa Implant will be utilized with the implant of the invention.

There are also preferably formed a pair of holes 22 at the base of each of the mounds 14 interiorly of the mounds 14. These holes also allow the ingrowth of fibrous tissue, but can be used to anchor adjacent muscles with sutures, if desired. As illustrated best in FIG. 1, openings 22 are interconnected to permit the insertion of sutures.

Figure 5:
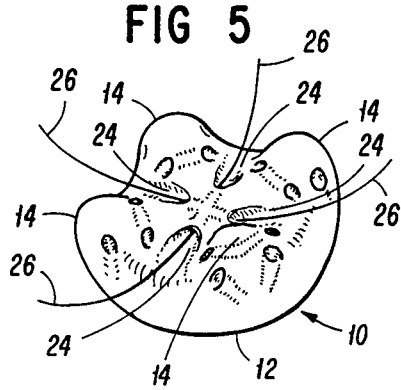
FIG. 5 is a perspective view of the implant similar to FIG. 1 and showing the sutures through the central holes prior to start of the implantation surgical procedure.

As best seen in FIGS. 1 and 5, there are also central openings 24, a pair of such openings being formed in the vertical valley 16 and a similar pair being formed in the horizontal valley 18. The pair of openings 24 formed in valley 16 are joined to permit the insertion of a suture, and similarly, the pair of openings 24 formed in the horizontal valley 18 are joined to permit the insertion of a suture. This is illustrated in FIG. 5.

The procedures for implanting the implant of the invention will now be described. After the implant is gas sterilized, it is rinsed with sterile distilled water or saline solution before use. The conjunctiva and Tenon's capsule are incised down to the sclera as close as possible to the cornea using Westcott scissors. With these two tissue layers held away from the globe, Stevens scissors are inserted and spread into each quadrant between the muscles in order to free the adhesions of Tenon's capsule from the globe. A muscle hook is then passed beneath a rectus muscle with is then severed from the globe being careful to avoid any cleaning of Tenon's capsule or adhesions. All rectus muscles are severed in this manner, but it is very important that Tenon's and intramuscular septum are not cleaned from the muscle insertion site. A stump of the medial or lateral rectus muscle may be left on the globe to facilitate grasping the globe for cutting the optic nerve stump, or a suture passed into the insertion site of one of the rectus muscles works equally well. Inferior and superior oblique muscles are detached from the globe prior to its removal. The globe is gently pulled anteriorly, and enucleation scissors are used to gently spread the tissue in each quadrant and sever any remaining adhesions between the globe and Tenon's capsule. The scissors are then place posteriorly to the globe and used to spread the tissue on either side of the optic nerve, which frees the posterior pole of the globe. The closed scissors are used to strum the optic nerve. The scissors are then opened, and one blade is placed on either side of the optic nerve and the nerve is severed. Any remaining tissue attachments are severed as close to the globe as possible as it is delivered. All active bleeding is then stopped by pressure application with a tamponade wrapped in gauze.

Figure 6:
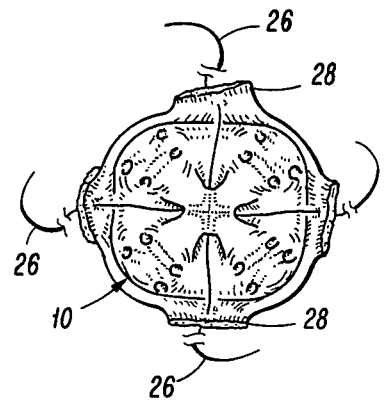
FIG. 6 is a plan view showing the implant centrally-placed with the pre-placed sutures engaging each of the vertical rectus muscles at the severed end of their tendons.

With the enucleation procedure completed, a doublarm 4-0 or 5-0 chromic suture 26 is then passed through each pair of the central openings 24 as illustrated in FIG. 5. The implant is then placed into Tenon's capsule and properly oriented with the vertical valley 16 vertical and the horizontal valley 18 horizontal. Each arm of the vertically oriented replaced suture 26 is then used to engage each of the vertical rectus muscles 28 at the severed ends of their tendons as shown in FIG. 6. Each arm of the horizontally replaced suture 26 is then engaged with the horizontal rectus muscles 30 in a similar fashion as illustrated in FIG. 6.

Figure 7:
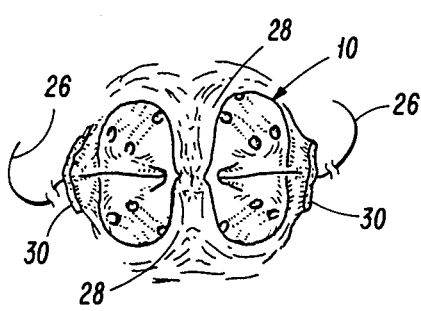
FIG. 7 is a view similar to FIG. 6 but showing the vertical muscles closed by tying the arms of the vertically-oriented sutures.
Figure 8:
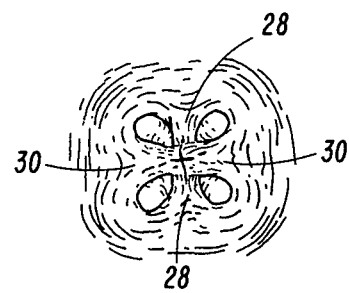
FIG. 8 is a view similar to FIG. 7 but showing the horizontal rectus muscles closed in a fashion similar to the vertical muscles using the pre-placed sutures.
Figure 9:
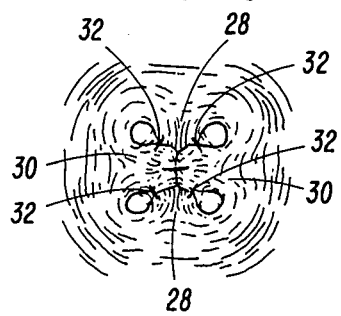
FIG. 9 is a view similar to FIG. 8 and illustrating the placement of sutures through holes in the implant and the adjacent muscle bellies to tie them together.

Once the vertical rectus muscles 28 are closed as shown in FIG. 7 by tying the arms of the vertically oriented sutures 26, the horizontal rectus muscles 28 are closed in a similar fashion as shown in FIG. 8. An additional one or two interrupted sutures can be used to secure the stumps of the vertical rectus muscles 28 to each other and the stumps of the horizontal rectus muscles 30 to each other as illustrated in FIG. 8. For further stabilization of the muscle, sutures 32 can be passed through the openings 22 at the base of each mound 14 and the adjacent muscle bellies tied together as illustrated in FIG. 9. However, this is usually not necessary since the muscles are commonly well-approximated. In any event, the additional sutures tied through the openings 22 to base of mounds 14 is in the discretion of the surgeon.

Figure 10:
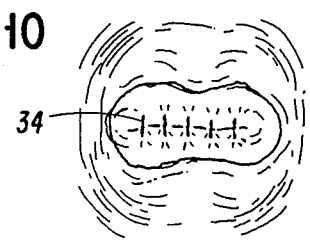
FIG. 10 is a view similar to FIG. 9 but showing the closure of Tenon's capsule using multiple interrupted sutures.
Figure 13:
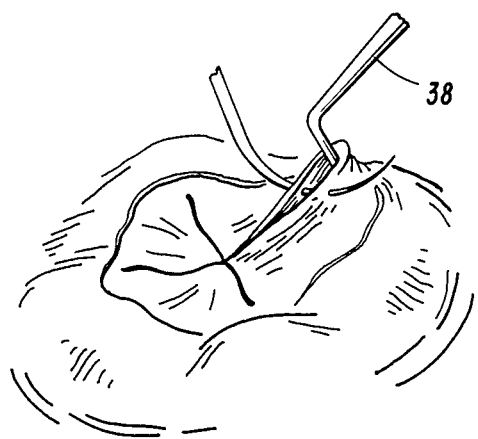

The proper and complete closure of Tenon's capsule is the most important factor in the permanence of the implant. Tenon's capsule can be closed quickly and completely with multiple interrupted 5-0 polyglacton sutures 34 as shown in FIG. 10. Although more complex, for those surgeons used to working with the Iowa Implant, the cruxiate closure may also be used. This technique is illustrated in FIGS. 12, 13 and 14 and theoretically helps to reduce the tension of Tenon's capsule over the mounds of the implant resulting in an increased chance of retention and better motility. To employ this technique of the cruxiate closure, any two arms of sutures 36 from the muscle imbrication are saved. With one arm, a bite approximately 4.0 mm in length is taken just back from the edge of Tenon's capsule at the 12 o'clock position. Then skipping, an identical bite is taken from the 3 o'clock or 9 o'clock positions. With the other arm of suture 36, a bite is taken at the 6 o'clock position and, skipping, another is taken in the remaining quadrant. This is all illustrated in FIG. 12. The arms are then tied to each other and Tenon's tissue is now drawn down against the center of the imbricated muscles. As illustrated in FIGS. 13 and 14, four small openings will remain, each in line with a mound 14. A muscle hook 38 is used to direct the openings toward their respective mounds 14 while interrupted sutures 40 close the loops.

Figure 11:
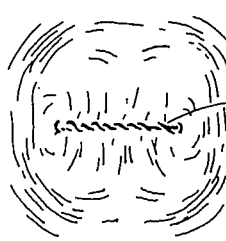
FIG. 11 is a view similar to FIG. 10 illustrating the completed implant procedure in which the conjunctiva is closed horizontally with sutures.

Regardless of which of the foregoing techniques is used, the conjunctiva is closed horizontally with running 6-0 chromic or plain cat-gut sutures 42 as shown in FIG. 11. Closure other than horizontal reduces the width of the cul-de-sac, and limits the horizontal movement of the prosthesis.

If an evisceration is done, the implant of the invention can also be used and gives rise to an excellent motility. After completing the standard evisceration procedure of one's choice, the implant is placed into the scleral shell. The cornea is removed and the proper size implant is placed into positon. The scleral edges are then sutured together using interrupted 5-0 vicryl sutures. Conjunctiva is then closed in the standard fashion.

Following placement of the implant, preferably the traditional, transparent acrylic conformer is placed in the socket upon the completion of the surgery. The conformer is immediately placed in the socket, and a monocular pressure dressing is applied as firmly as possible to reduce swelling. The dressing is generally removed 5 days after surgery and the patient is fitted with a prosthesis six to eight weeks after surgery. Preferably, the prosthetic fitting of this implant is best done by a standard modified impression technique.

It will be understood from the foregoing description of the implant of the invention, that the implant has numerous advantages over prior art implants. With the ball implants, migration is the most common problem and can be compounded when surgeons imbricate the extraocular muscles in an effort to obtain better motility. With the quasi-integrated implants, such as the Iowa Implant, extrusion and time consuming surgical techniques required for implantation have been major criticisms. The implant of the invention is not as easy to insert as a ball implant, but it has several other beneficial features. For example, the implant of the invention utilizes a faster surgical technique for implantation and avoids having to clean the muscles. The implant of the invention has lower, more rounded mounds that should greatly decrease the later extrusion rate of prior art implants. Since the implant of the invention has a larger girth and larger radius of its posterior surfaces, these will support the fat and other orbital tissues better than prior art implants which results in a more natural superior sulcus. Also, the implant of the invention can be used either as an evisceration implant or a secondary implant and is thus a truly universal implant. Obviously, the implant of the invention has a greater degree of motility than the standard ball implant but is as easy to implant surgically.

Having thus described the invention in connection with the preferred embodiment thereof, it will be evident to those skilled in the art that various revisions and modifications can be made to the preferred embodiment without departing from the spirit and scope of the invention. It is my intention however that all such revisions and modifications as are evident to those skilled in the art will be included within the scope of the following claims.

What is claimed is:

1. An implant for use with a prosthetic eye comprising a main body having top and bottom edges that are straight across and parallel to each other joined by rounded corners to sides that are straight and parallel to each other to form a substantially square configuration that has an anterior portion and a smooth convex posterior surface, a plurality of circumferentially-spaced outwardly-tapered mounds forming a part of the anterior portion, a mound being located at each of the rounded corners of the main body and terminating in a rounded extremity, the anterior portion also having formed between the mounds shallow valleys to accommodate the severed ends of the four rectus muscles of the eye during the implant procedure, one valley extending between the top and bottom edges and the other valley extending between the sides of the main body, the two valleys crossing at the center of the anterior portion to form a relatively flat central portion, and a pair of interconnected suture holes formed in each of the valleys in the central portion to provide for securing the ends of the rectus muscles to each other and to the implant.

2. The implant of claim 1 in which there is provided at the base of each of the mounds along the inside surface near the central portion of the main body a pair of interconnected suture holes to receive sutures or not depending upon the decision of the surgeon performing the implant procedure.

3. The implant of claim 1 in which the height of the mounds above the valleys are relatively low, and the mounds slope very gradually into the valleys.

4. The implant of claim 3 in which all the exterior surfaces of the implant are smooth and curved.

* * * * *